United States Patent [19]
Cohn et al.

[11] Patent Number: 5,767,113
[45] Date of Patent: Jun. 16, 1998

[54] COMPOUNDS USEFUL FOR CONCURRENTLY ACTIVATING GLUCOCORTICOID-INDUCED RESPONSE AND REDUCING MULTIDRUG RESISTANCE

[75] Inventors: Suzanne Bourgeois Cohn; Donald J. Gruol, both of Del Mar, Calif.

[73] Assignee: The Salk Institute For Biological Studies, La Jolla, Calif.

[21] Appl. No.: 438,887

[22] Filed: May 10, 1995

[51] Int. Cl.$^6$ .......................... A61K 31/58; A61K 31/56; A61K 31/585

[52] U.S. Cl. .......................... 514/176; 514/188; 514/181; 514/177; 514/178; 514/179; 514/172; 514/174; 514/175

[58] Field of Search .................. 514/180, 181, 514/177, 178, 179, 172, 174, 175, 176

[56] References Cited

U.S. PATENT DOCUMENTS

| | | | |
|---|---|---|---|
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |
| 4,386,085 | 5/1983 | Teutsch et al. | 424/238 |
| 4,923,871 | 5/1990 | Inaba et al. | 514/255 |
| 4,990,538 | 2/1991 | Harris et al. | 514/648 |
| 5,104,858 | 4/1992 | Hait et al. | 514/34 |
| 5,114,919 | 5/1992 | Baldwin et al. | 514/11 |
| 5,132,299 | 7/1992 | Ottow et al. | 514/169 |
| 5,160,727 | 11/1992 | Klohs et al. | 424/10 |
| 5,173,486 | 12/1992 | Monkovic et al. | 514/211 |
| 5,182,293 | 1/1993 | Sunkara et al. | 514/340 |
| 5,190,957 | 3/1993 | Sunkara et al. | 514/314 |
| 5,198,344 | 3/1993 | Croop et al. | 435/69.1 |

FOREIGN PATENT DOCUMENTS

| | | |
|---|---|---|
| WO 90/15599 | 12/1990 | WIPO . |
| WO 92/11034 | 7/1992 | WIPO . |
| WO 92/13551 | 8/1992 | WIPO . |
| WO 92/18089 | 10/1992 | WIPO . |
| WO 92/18131 | 10/1992 | WIPO . |
| WO 93/00064 | 1/1993 | WIPO . |
| WO 93/03729 | 3/1993 | WIPO . |

OTHER PUBLICATIONS

Dalton et al, *Medline Abstracts*, Abstract No. 89177422, 1989.

Danel–Moore et al, *Medline Abstracts*, Abstract No. 94097061, 1992.

Agarwal and Khorana "Studies on Polynucleotides. CII. The Use of Aromatic Isocyanates for Selective Blocking of hte Terminal 3'-Hydroxyl Group in Protected Deoxyribooligonucleotides" *J. Am. Chem. Soc.* 94:3578–3585 (1972).

Barton et al. "Hypophosphorous Acid and its Salts: New Reagents for Radical Chain Deoxygenation, Dehalogenation and Deamination" *Tetrahedron Letters* 33:5709–5712 (1992).

Barton et al. "The Invention of Radical Reactions. Part XXIV.[1] Relative Rates of Acylation and Radical Deoxygenation of Secondary Alcohols" *Tetrahedron* 48:7435–7446 (1992).

Boden and Keck "Proton–Transfer Steps in Steglich Esterification: A Very Practical New Method for Macrolactonization" *J. Org. Chem.* 50:2394–2395 (1985).

Efferth and Volm "Rapid Detection Assays for Multidrug Resistance" *Arzneim–Forsch* 38:1771–1774 (1988).

Ford and Hait "Pharmacology of Drugs That Alter Multidrug Resistance in Cancer" *Pharmacological Reviews* 42:155–199 (1990).

Goodman and Gilman *The Pharmacological basis of Therapeutics*, (7th ed.) pp. 1277–1280 (1985).

Gottesman and Pastan "The Multidrug Transporter, a Double–edged Sword" 263:12163–12166 (1988).

Herweijer et al. "A Rapid and Sensitive Flow Cytometric Assay for the Detection of Multidrug Resistant Cells in Human Cancer" *Invest. New Drugs* 7:442 (1989).

Konen et al. "The Multidrug Transporter: Rapid Modulation of Efflux Activity Monitored in Single Cells by the Morphologic Effects of Vinblastine and Daunomycin" *J. Histochem. Cytochem.* 37:1141–1145 (1989).

Neises and Steglich "Simple Method for the Esterification of Carboxylic Acids" *Agnew. Chem., Int. Ed. Engl.* 17:522–524 (1978).

Neises and Steglich "Esterification of Carboxylic Acids with Dicyclohexyl–Carbodiimide/4–Dimethylaminopyridine: tert–Butyl Ethyl Fumarate" *W. Org. Synth.* 63:183–187 (1984).

Stewart and Evans "Non–chemotherapeutic agents that potentiate chemotherappy efficacy" *Cancer Treatment Reviews* 16:1–40 (1989).

Twentyman et al. "The in vitro effects and cross–resistance patterns of some novel anthracyclines" *Br. J. Cancer* 53:585–594 (1986).

Yoshimura et al. "Novel screening method for agents that overcome classical multidrug resistance in a human cell line" *Cancer Letters* 50:45–51 (1990).

Teutsch et al.. "11β–Substituted Steroids, An Original Pathway to Antihormones" *J. Steroid Biochem.* 31(4B):549–565 (1988).

*Primary Examiner*—William R.A. Jarvis
*Attorney, Agent, or Firm*—Gray Cary Ware & Freidenrich; Stephen E. Reiter

[57] ABSTRACT

In accordance with the present invention, it has been discovered that certain synthetic steroid compounds are capable of inhibiting the efflux pump which is believed to be responsible for multidrug resistance, while at the same time activating glucocorticoid-induced response. Thus, chemotherapy of glucocorticoid sensitive tumors can be enhanced by use of a compound having the dual ability to activate glucocorticoid-induced response and facilitate the accumulation of drug at the target site, with reduced or eliminated competition by the drug efflux system.

24 Claims, 2 Drawing Sheets

COMPOUNDS USEFUL FOR CONCURRENTLY ACTIVATING GLUCOCORTICOID-INDUCED RESPONSE AND REDUCING MULTIDRUG RESISTANCE

FIELD OF THE INVENTION

The present invention relates to methods for the treatment of multidrug resistance. In another aspect, the present invention relates to methods of enhancing the intracellular accumulation of molecules within a cell. In yet another aspect, the present invention relates to methods of activating glucocorticoid-induced response, while at the same time reducing multidrug resistance.

BACKGROUND OF THE INVENTION

The treatment of human tumors with cytotoxic drugs is an important part of modern clinical cancer therapy. However, effective tumor treatment is frequently thwarted by the lack of sensitivity of certain tumors to standard chemotherapeutic agents (intrinsic resistance) or by the ability of certain tumors to develop chemotherapeutic resistance during the course of treatment (acquired resistance). The cause of this phenomenon has, at least in part, been demonstrated to result from the existence of an energy-dependent efflux pump which acts to remove the chemotherapeutic agent from the target cell.

The pump consists of P-glycoprotein found as a constituent of the cell membrane. It has been suggested that the normal function of P-glycoprotein is to remove toxins from within the cell. This theory is supported by the observation that P-glycoprotein is found as a cell membrane constituent in cells such as liver, kidney, colon, and jejunum. It has also been suggested that P-glycoprotein in the cell membrane of normal tissues could act to remove toxins or to assist in the transport of nutrients and solutes, and in secreting a variety of protein and steroid substances. The natural presence of P-glycoprotein in tumor cells derived from these tissues, as well as its presence in tumor cells derived from other tissue types could explain, at least in part, resistance of various tumors to therapy with standard chemotherapeutic agents. Indeed, cancer cells demonstrate cross resistance to a diverse group of lipophilic drugs with unrelated structures and functions, a phenomenon known as multidrug resistance (MDR).

Drugs of proven antitumor chemotherapeutic value to which multidrug-resistance has been observed include vinblastine, vincristine, etoposide, teniposide, doxorubicin (adriamycin), daunorubicin, plicamycin (mithramycin), actinomycin D and taxol. Many tumors are intrinsically multidrug-resistant (e.g., adenocarcinomas of the colon and kidney) while other tumors acquire multidrug-resistance during therapy (e.g., neuroblastomas and childhood leukemias).

Several strategies have been devised to circumvent clinical MDR. One promising approach is the utilization of chemosensitizing agents which can inhibit active efflux of drugs in resistant cells. Numerous compounds including calcium antagonists, calmodulin inhibitors, and some drug analogues have shown variable abilities to reverse MDR. Most of these agents are lipophilic and may act as a ligand for the P-glycoprotein (i.e., bind to P-glycoprotein), thereby competitively inhibiting its drug efflux effect. Excellent reviews have recently been published on agents that alter multidrug resistance in cancer. See, for example, James M. Ford and William N. Hait, Pharmacology of Drugs that Alter Multidrug Resistance in Cancer, *Pharmacological Reviews* 42:155–199 (1990); David J. Steward and William K. Evans, Non-Chemotherapeutic Agents that Potentiate Chemotherapy Efficacy, *Cancer Treatment Reviews* 16:1–40 (1989).

The major factor thus far limiting the use of certain MDR reversing agents in cancer patients is the toxicity of such reversing agents, which prevents them from reaching effective concentrations during treatment. Another factor limiting the use of MDR reversing agents is the occurrence of undesired side effects caused by the agent employed. One way to enhance the effect of chemotherapy is to design compounds which have the ability to both reverse multidrug resistance and which also have therapeutic effect(s). For example, glucocorticoid receptor agonists function as immunosuppressive agents, and are effective for killing lymphomas. Compounds which have both MDR reversing properties and glucocorticoid receptor agonist properties, therefore, would be highly desirable agents for the treatment of a variety of disease states.

Thus, a substantial challenge remains in the search for ideal MDR reversing agents, i.e., agents which are pharmacologically acceptable for clinical applications, and which are more potent, but less toxic (and/or promote fewer side reactions and/or have a plurality of functional properties) than reversing agents employed in the prior art.

BRIEF DESCRIPTION OF THE INVENTION

In accordance with the present invention, we have discovered that certain synthetic steroid compounds are capable of inhibiting the efflux pump which is believed to be responsible for multidrug resistance, while at the same time acting as agonists for the glucocorticoid receptor. Thus, chemotherapy can be enhanced by facilitating the delivery of drug to the target site, with reduced or eliminated competition by the drug efflux system. Compounds employed in the practice of the present invention inhibit the drug efflux pump, and also display substantial affinity for the glucocorticoid receptor. Thus, invention compounds, in addition to inhibiting the drug efflux pump, are also capable of inducing a glucocorticoid-mediated therapeutic response, because glucocorticoids are toxic to certain cells. Thus such compounds can advantageously be used in glucocorticoid sensitive tumor cells.

Invention compounds are especially useful in combination therapies where a glucocorticoid is administered in combination with other therapeutic agents, e.g., an antineoplastic agent. The combination is particularly effective because invention compounds are capable of serving two functions, i.e., acting as a glucocorticoid receptor agonist, and also facilitating delivery of anti-neoplastic agents to the target site (because the drug efflux pump is inhibited by invention compounds).

In accordance with another aspect of the present invention, we have developed assays for the identification of compounds that have the dual ability to reverse multidrug resistance, while at the same time acting as agonists for the glucocorticoid receptor. Invention assays allow the identification of additional compounds which are useful in the methods described herein.

BRIEF DESCRIPTION OF THE FIGURES

FIG. 1 presents the results of an evaluation of the glucocorticoid agonist activity of several steroid analogs. The glucocorticoid-induced apoptosis of murine thymoma W7TB cells was taken as a measure of the agonist activity of steroid analogs. Murine W7TB cells were distributed (5×10⁴ cells/ml/well) into multiwell dishes and incubated for 5 days with increasing concentrations of test compound, as indicated in the Figure. At the end of the incubation period, the turbidity values (at 660 nm) for each set of cultures were measured and expressed relative to cells that were incubated without test compound. These values represent the effect of test compound on the relative amount of cell proliferation under a given set of growth conditions. Each value shown in the Figures is the average of 2 separate determinations.

FIG. 2 presents the results of an evaluation of the ability of several steroid analogs to reverse multidrug resistance in test cells. Human CEM/VLB$_{100}$ cells were distributed (5×10⁴ cells/ml, 1 ml/well) into multiwell dishes and incubated for 5 days with 30 nM vinblastine and increasing concentrations of test compound, as indicated in the Figure. At the end of the incubation period, the turbidity values (at 660 nm) for each set of cultures were measured and expressed relative to cells that were incubated without test compound. These values represent the ability of test compound, relative to control (i.e., verapamil) to reverse CEM/VLB$_{100}$ resistance to 30 nM vinblastine, as reflected by the relative amount of cell proliferation under a given set of growth conditions. Each value shown in the Figures is the average of 2 separate determinations.

DETAILED DESCRIPTION OF THE INVENTION

Figure 1A:
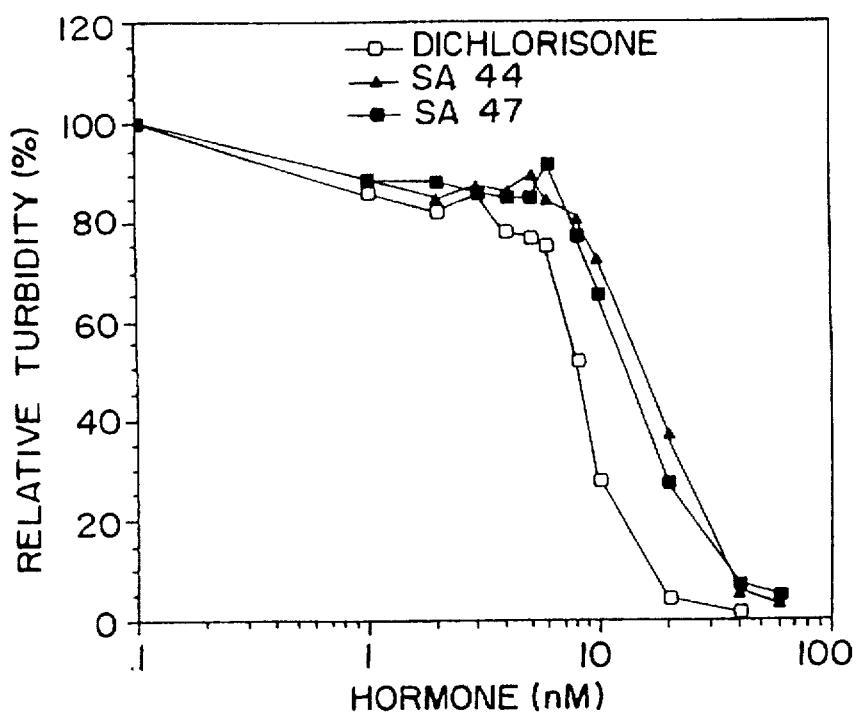
FIG. 1A presents results with the agonist, dichlorisone, as well as 2 derivatives thereof.

In accordance with the present invention, there is provided a method for concurrently activating glucocorticoid-induced response and reducing multidrug resistance in a subject undergoing chemotherapy, said method comprising:

administering to said subject, in conjunction with a chemotherapeutic agent, an effective amount of a compound having the dual properties of acting as a glucocorticoid agonist and as an inhibitor of the P-glycoprotein efflux pump.

Compounds contemplated for use in the practice of the present invention include compounds having the structure:

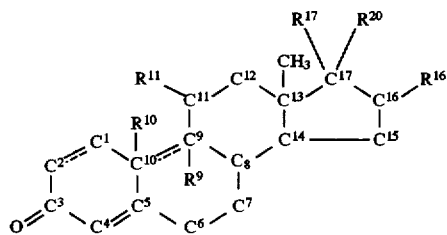

wherein:

$R^9$ is absent when there is a double bond between $C^9$ and $C^{10}$, or when there is an epoxide bridging $C^9$ and $C^{10}$, or when present, $R^9$ is selected from hydrogen or halogen;

$R^{10}$ is absent when there is a double bond between $C^9$ and $C^{10}$, or when there is an epoxide bridging $C^9$ and $C^{10}$, or when present, $R^{10}$ is selected from hydrogen or methyl;

$R^{11}$ is independently selected from hydrogen, alkenyl, alkynyl, halogen, or —OR, wherein R is selected from hydrogen, lower alkyl or trimethylsilyl;

$R^{16}$ is H or methyl, and $R^{17}$ is hydrogen or —OH, when $R^{20}$ is an organic radical having in the range of 4 up to 20 carbon atoms, wherein said organic radical optionally contains one or more atoms selected from oxygen, sulfur, nitrogen, phosphorus, silicon or halogen, wherein said organic radical optionally includes one or more cyclic moieties selected from alicyclic ring(s), heterocyclic ring(s), carbocyclic aromatic ring(s), or heterocyclic aromatic ring(s), wherein said cyclic moiety(ies) optionally contains an oxygen-, sulfur-, nitrogen-, phosphorus- or silicon-bearing substituent, wherein said cyclic moiety is mandatory when $R^{20}$ is linked to $C^{17}$ through a —C(O)— moiety; or $R^{17}$ is —OR', wherein R' is selected from hydrogen or an acyl group having in the range of 3 up to 20 carbon atoms, wherein said acyl group optionally contains one or more atoms selected from oxygen (in addition to the acyl carbonyl oxygen), sulfur, nitrogen, phosphorus, silicon or halogen, wherein said acyl group optionally includes one or more cyclic moieties selected from alicyclic ring(s), heterocyclic ring(s), carbocyclic aromatic ring(s), or heterocyclic aromatic ring(s), wherein said cyclic moiety(ies) optionally contains an oxygen-, sulfur-, nitrogen-, phosphorus- or silicon-bearing substituent, when $R^{20}$ is —C(O)—(CH$_2$)$_q$—Z, wherein q falls in the range of 0 up to 8, and Z is selected from alkyl, hydroxyalkyl, alkoxy, aryl or halogen.

Optionally, compounds employed in the practice of the present invention can have a double bond in the steroid "A" ring between $C^1$ and $C^2$, or a double bond in the steroid "B" ring between $C^9$ and $C^{10}$. Those of skill in the art recognize that substituents "$R^9$" and "$R^{10}$" will not be present when there is a double bond in the "B" ring. As an alternative to a carbon-carbon double bond between $C^9$ and $C^{10}$, an epoxide can also bridge these two carbons.

As employed herein, "lower alkyl" refers to straight or branched chain alkyl radicals having in the range of about 1 up to 4 carbon atoms; "alkyl" refers to straight or branched chain alkyl radicals having in the range of about 1 up to 12 carbon atoms; "substituted alkyl" refers to alkyl radicals further bearing one or more substituents such as hydroxy, alkoxy (of a lower alkyl group), mercapto (of a lower alkyl group), aryl, carboxyl, heterocyclic, halogen, trifluoromethyl, cyano, nitro, amino, carboxyl, carbamate, sulfonyl, sulfonamide, and the like;

"alkenyl" refers to straight or branched chain hydrocarbyl radicals having at least one carbon-carbon double bond, and having in the range of about 2 up to 12 carbon atoms and "substituted alkenyl" refers to alkenyl radicals further bearing one or more substituents as set forth above;

"alkynyl" refers to straight or branched chain hydrocarbyl radicals having at least one carbon-carbon triple bond, and having in the range of about 2 up to 12 carbon atoms, and "substituted alkynyl" refers to alkynyl radicals further bearing one or more substituents as set forth above;

"alicyclic" refers to cyclic (i.e., ring-containing) hydrocarbyl radicals having in the range of 3 up to 14 carbon atoms, and "substituted alicyclic" refers to alicyclic radicals further bearing one or more substituents as set forth above;

"heterocyclic" refers to cyclic (i.e., ring-containing) radicals containing one or more heteroatoms (e.g., N, O, S, or the like) as part of the ring structure, and having in the range of 3 up to 14 carbon atoms and "substituted heterocyclic" refers to heterocyclic radicals further bearing one or more substituents as set forth above;

"carbocyclic aromatic" refers to aromatic radicals having in the range of 6 up to 14 carbon atoms and "substituted aryl" refers to aryl radicals further bearing one or more substituents as set forth above;

"heterocyclic aromatic" refers to aromatic radicals containing one or more heteroatoms (e.g., N, O, S, or the like) as part of the ring structure, and having in the range of 3 up to 14 carbon atoms and "substituted heterocyclic aromatic" refers to heterocyclic aromatic radicals further bearing one or more substituents as set forth above;

"acyl" refers to alkyl-carbonyl species or substituted alkyl-carbonyl species; and "halogen" refers to fluoride, chloride, bromide or iodide radicals.

In a presently preferred aspect of the present invention, $R^9$ is a halogen.

In a presently preferred aspect of the present invention, $R^{10}$ is a methyl group.

In a presently preferred aspect of the present invention, $R^{11}$ is selected from hydrogen, hydroxy or halogen.

In a presently preferred aspect of the present invention, $R^{16}$ is methyl.

In a presently preferred aspect of the present invention, when $R^{20}$ is an organic radical having in the range of 4 up to 20 carbon atoms, as broadly defined above, $R^{17}$ is selected from hydrogen or hydroxy. Alternatively, when $R^{20}$ is more narrowly defined (i.e., —C(O)—(CH$_2$)$_q$—Z, as set forth above), $R^{17}$ is preferably —OR', wherein R' is selected from —C(O)—(CH$_2$)$_q$—Ar or —C(O)—NH—(CH$_2$)$_q$—Ar, wherein q falls in the range of about 0 up to 8 and Ar is as defined hereinbelow.

In one aspect of the present invention, $R^{20}$ includes one or more rings independently selected from carbocyclic aromatic ring(s) or heterocyclic aromatic ring(s). Optionally, such aromatic ring(s) further contains at least one oxygen-, sulfur-, nitrogen-, phosphorus- and/or silicon-bearing substituent.

In a particular aspect of the present invention, $R^{20}$ is selected from:

—C(O)—CH$_2$—O—C(O)—(CH$_2$)$_q$—Ar

—C(O)—CH$_2$—O—C(O)—NH—(CH$_2$)$_q$—Ar, wherein q falls in the range of about 0 up to 8 and Ar is:

—(C$_6$H$_x$)—[X$_{0,1}$—(CH$_2$)$_y$—X']$_z$ wherein:

x is 2–5, y is 0–2, z is 0 when x is 5, i.e., when the aromatic ring is C$_6$H$_5$, or 1 when x is 4, i.e., when the aromatic ring is C$_6$H$_4$, or 2 when x is 3, i.e., when the aromatic ring is C$_6$H$_3$, or 3 when x is 2, i.e., when the aromatic ring is C$_6$H$_2$.

X is O or S, and

X' is R when y is O, wherein R is as defined above, or

X' is hydrogen, OR, NR"$_2$, N$^+$R"$_3$,

or NO$_2$, when y is 1 or 2, wherein R is as defined above and R" is hydrogen or lower alkyl.

When z of the above general formula is 1, the substituent on the phenyl ring is preferably located at the para position of the ring. Especially preferred para substituents include:

—O—CH$_2$CH$_2$—NR"$_2$, —O—CH$_2$CH$_2$—N$^+$R"$_3$,

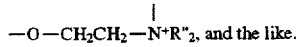, and the like.

When z of the above general formula is 2, the substituents on the phenyl ring are preferably located at the meta and para positions of the ring, wherein the preferred para substituents are selected from OR, NR"$_2$,

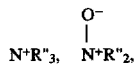

or NO$_2$. Exemplary aromatic species contemplated by the above include phenyl, 3,4-dimethoxyphenyl, 3,4,5-trimethoxyphenyl, 4-dimethylaminophenyl, N-methyl piperazine, and the like.

In another aspect of the present invention, $R^{20}$ is selected from:

—(CH$_2$)$_x$—CR"=CR"—(CH$_2$)$_x$—X"

or

—(CH$_2$)$_x$—C≡C—(CH$_2$)$_x$—X", wherein R" is selected from hydrogen and lower alkyl, and X" is selected from hydrogen, chloro, trimethylsilyl or a cyclic moiety selected from an optionally substituted alicyclic ring, heterocyclic ring, carbocyclic aromatic ring, or heterocyclic aromatic ring, and each x is independently selected from 0–6, with the proviso that $R^{20}$ contain at least 6 carbon atoms.

Presently preferred compounds of the invention are those wherein:

$R^9$ is chlorine or fluorine;

$R^{10}$ is methyl;

$R^{11}$ is chlorine or hydroxy;

$R^{16}$ is methyl;

$R^{17}$ is hydrogen or hydroxy; and $R^{20}$ is selected from:

—C(O)—CH$_2$—O—C(O)—(CH$_2$)$_q$—Ar or

—C(O)—CH$_2$—O—C(O)—NH—(CH$_2$)$_q$—Ar, wherein Ar is selected from phenyl, 3,4-dimethoxyphenyl, 3,4,5-trimethoxyphenyl, 4-dimethylaminophenyl, or N-methyl piperazine, and q falls in the range of about 0 up to 8.

The compounds of the present invention are capable of enhancing the sensitivity of multidrug resistant tumor cells to antitumor chemotherapeutic agents, while at the same time acting as agonists for glucocorticoid receptors. In addition, the compounds of the present invention are useful in preventing the emergence of multidrug resistant tumor cells during a course of treatment with antitumor chemotherapeutic agents. The compounds of the present invention are further useful in reducing the effective dosage of chemotherapeutic agent required during treatment of multidrug resistant tumors.

Clinical multidrug resistance can develop in response to a number of important chemotherapeutic agents, including vinblastine (0.1 mg per kilogram per week), vincristine (0.01 mg per kilogram per week), dactinomycin (0.015 mg per kilogram per day), daunorubicin (60 to 75 mg per square meter per week), doxorubicin (500 to 600 mg per square meter), etoposide (35 to 50 mg per square meter per day), and mithramycin (0.025 mg per kilogram per day). Multidrug resistance has been shown to occur in vitro as well as in the clinic.

In accordance with another embodiment of the present invention, there are provided methods for identifying compounds which have the concurrent ability to activate glucocorticoid-induced response and reduce multidrug resistance in a subject undergoing chemotherapy. The invention assay comprises:

monitoring the accumulation of a detectable reagent by a drug resistant cell line when contacted with a test compound and said detectable reagent, monitoring the glucocorticoid-induced response when a glucocorticoid-sensitive cell line is contacted with said test compound; and thereafter selecting compounds which increase the accumulation of test compound into drug resistant cells and induce glucocorticoid-mediated response.

Those of skill in the art can readily identify detectable reagents which are suitable for use in the invention assay. For example, radioactively labelled compounds can be used, having the benefit of being readily detected. In addition, dyes (e.g., Rhodamine 123), anthracyclines (e.g., daunomycin), and the like, can also be employed.

Cell lines useful for detecting glucocorticoid-induced response are well known and readily available to those of skill in the art. For example, murine thymoma cells are induced to undergo apoptosis in the presence of glucocorticoids, thus making detection of glucocorticoid response quite simple.

Multidrug resistant cell lines are easily developed for in vitro determination of the ability of compounds of the present invention to reduce multidrug resistance. Such cell lines can be readily developed in accordance with the methods described by Twentyman et al., Br. J. Cancer 54:253 (1986). The Twentyman procedure selects for multidrug resistant cells by culturing the parental drug sensitive cell line in the continued presence of a cytotoxic drug, for example, doxorubicin.

Drug sensitive cells will perish because of their inability to prevent accumulation of drug into the cell. In contrast, multidrug resistant cells will survive and grow, despite the presence of the drug (because of their ability to pump drug away from its intracellular target). Eventually, a multidrug resistant cell population emerges and can be used in an assay system for the detection of agents which can modify the multidrug resistance. Many cell lines are suitable as parental cell lines from which multidrug resistant cells can be selected. These cell lines can be derived from humans or other mammals and can be derived from normal tissue or tumor tissue. Commercially available human cell lines derived from human tumor tissue include KB (ATCC CCL 17), NCI-H69 (ATCC HTB 119), CCRF-CCM (ATCC CCL 119), and K-562 (ATCC CCL 243). Other suitable, commercially available mammalian cell lines include LM(TK-) (ATCC CCL 1.3), and CHO-K1 (ATCC CCL 61).

The sensitivity of drug resistant cell lines to chemotherapeutic agents can be compared with the parental cell line by assaying inhibition of cell growth during continuous exposure to the drug. Growth of the parental cells will be inhibited by the chemotherapeutic agent, while the growth of resistant cells will not be inhibited. Cell growth can be measured by cell counting using an electronic cell counter, for example, a Coulter Counter, Coulter Electronics, Herts, England, and following the manufacturers recommended instructions for use. Cells may also be counted microscopically using a hemocytometer. The presently preferred technique is to combine the use of the hemocytometer with a stain (e.g., tryptan blue) that allows one to distinguish between living cells and dead cells.

Cell growth can also be measured by other techniques including cell staining. Cells can be stained by various agents including crystal violet, coomassie blue and methylene blue, with methylene blue being the presently preferred stain. Determining cell growth by methylene blue staining can be done as described in Example 1, below.

Cell growth measured by either the cell counting method or the cell staining method should closely correlate. The staining method is preferable because of its simplicity and it is easily adaptable to automation which allows many experiments to be performed with many test compounds non-labor intensively.

Radiolabelled compounds may also be utilized to determine the accumulation of antitumor chemotherapeutic agents in drug sensitive cells and in multidrug resistant cells. For example, the accumulation of [$^3$H]vinblastine by drug sensitive cell lines and drug resistant cell lines in the presence or absence of compound(s) of the invention may be determined. The relative accumulation of the radiolabelled chemotherapeutic agent is indicative of the ability of a compound of the invention to reduce multidrug resistance.

The modulation of multidrug resistance demonstrated by the compounds described herein provides a method for treatment of multidrug resistant tumors. The multidrug resistant modulating properties of the compounds described herein also provide a method for preventing the emergence of multidrug resistant tumors during the course of cancer treatment. These same compounds additionally provide a method for reducing the required dosage of an antitumor chemotherapeutic agent.

Compounds employed in the practice of the present invention have the added property of acting as glucocorticoid receptor agonists. Thus, invention compounds are particularly useful for treatment of tumors which are sensitive to glucocorticoid receptor agonists. In such situations, invention compounds (acting as glucocorticoid receptor agonists) directly attack the abnormal cells being targetted for treatment and also (acting as MDR reversing agents) facilitate transport of supplemental antineoplastic agents to the cellular target thereof.

All of the treatment methods of the present invention involve (1) the administration of a compound of the present invention, prior to or concurrent with the optional further administration of a chemotherapeutic agent; or (2) the administration of a combination of one or more of the compounds of the present invention, and an antitumor chemotherapeutic agent.

Reference to administering compounds contemplated for use in the practice of the present invention "in conjunction with" a chemotherapeutic agent or "concurrently administering," compounds according to the present invention, as used herein, means that the antineoplastic agent and the agent employed for the reduction of multidrug resistance are administered either (a) simultaneously in time (optionally by formulating the two together in a common carrier), or (b) at different times during the course of a common treatment schedule. In the latter case, the two agents are administered at times sufficiently close for the agent employed for reducing multidrug resistance to enhance the selective growth-inhibiting action of the antineoplastic agent on the tumor cells.

For the treatment of multidrug resistant tumor cells, the compounds of the present invention (either separately or in combination with a chemotherapeutic agent), may be administered in any of a variety of ways, as can be readily identified by those of skill in the art, such as, for example, orally, parenterally (including subcutaneous injection, intravenous, intramuscular, intrasternal injection or infusion techniques), percutaneously, rectally, by inhalation, and the like, in dosage unit formulations containing conventional non-toxic, pharmaceutically-acceptable carriers, adjuvants and/or vehicles.

The compounds of the present invention may be administered to a subject either separately or in combination with an appropriate chemotherapeutic agent such as vinblastine, vincristine, dactinomycin, daunorubicin, doxorubicin, etoposide, mithramycin, taxol, and the like. The term "subject," as used herein, is taken to mean mammals such as primates, including humans, sheep, horses, cattle, pigs, dogs, cats, rats and mice.

The pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound (i.e., the above-described glucocorticoid agonist/multidrug resistance-reducing compounds) is included in the pharmaceutical composition in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

Oily suspensions may be formulated by suspending the active ingredient in a vegetable oil, for example, arachis oil, olive oil, sesame oil or coconut oil; in a mineral oil such as liquid paraffin; in a cremaphor such as castor oil; and the like. The oily suspensions may contain a thickening agent, for example, beeswax, hard paraffin or cetyl alcohol. Sweetening agents and flavoring agents may be added to provide a palatable oral preparation. These compositions may be prepared by the addition of an antioxidant such as ascorbic acid.

Pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Pharmaceutical compositions of the invention may also be prepared in the form of a sterile injectable suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives antioxidants and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

Typical daily dosage levels, in general, for the reduction of multidrug resistance lies within the range of from about 0.5 µg to about 10 mg per kg body weight and, preferably within the range of from 50 µg to 1 mg per kg body weight and can be administered up to four times daily. The daily IV dose for the reversal of multidrug resistance lies within the range of from about 1 µg to about 10 mg per kg body weight and, preferably, within the range of from 10 µg to 500 µg per kg body weight.

For the treatment of multidrug resistant tumors, the compounds of the present invention may be utilized to sensitize multidrug resistant tumor cells to chemotherapeutic agents and also to reduce the effective dosage of a chemotherapeutic agent during the course of treatment. For these purposes, the compounds of the present invention may be utilized in combination with one or more chemotherapeutic agents which are useful in treating cancer selected from the group consisting of: vinblastine, vincristine, dactinomycin, daunorubicin, doxorubicin, mithramycin, bleomycin, actinomycin D, etoposide, teniposide, taxol and mitomycin-C, as well as combinations of such agents, or salts or other derivative forms thereof. The compounds of the present invention may be administered in combination with, in conjunction with, prior to or concurrent to the administration of chemotherapeutic agents.

The weight ratio of a compound of the present invention to chemotherapeutic agent or compound may vary and will depend upon the effective dose of each ingredient. Generally, an effective dose of each ingredient (i.e., chemotherapeutic agent and MDR-reducing compound) will be used. Thus, for example, when a compound of the present invention is combined with a chemotherapeutic agent (as set forth above), the weight ratio of the compound of the present invention to chemotherapeutic agent ranges from about 1000:1 to about 1:1000, preferably about 100:1 to 1:100. Combinations of a compound of the present invention and an anticancer agent or compound will generally also be within the aforementioned range, but in each case, an effective dose of each active ingredient should be used.

The compounds contemplated for the use in the practice of the present invention possess the dual activity of increasing the sensitivity of multidrug resistant mammalian cells to chemotherapeutic agents in culture, and are useful in the treatment of multidrug resistant tumors in mammalian subjects. Indeed, invention compounds are especially useful for the treatment of tumors which are susceptible to glucocorticoid receptor agonists.

Thus, tumors which can be treated by the method of the present invention include both benign and malignant tumors or neoplasms, and include melanomas, lymphomas, leukemias, and sarcomas. Illustrative examples of tumors are glucocorticoid-sensitive tumors where combination therapy is commonly used. Of course those tumors which typically are or become multidrug resistant are most beneficially treated with the method of the present invention, since invention compounds provide the dual function of glucocorticoid agonist (with its attendant therapeutic affect) and MDR-reversing agent. Examples include cutaneous tumors, such as malignant melanomas and mycosis fungoides; hematologic tumors such as leukemias, for example, acute lymphoblastic, acute myelocytic or chronic myelocytic leukemia; lymphomas, such as Hodgkin's disease or malignant lymphoma. The effective amount of chemotherapeutic agent used in the method of the present invention varies widely and depends on factors such as the patient, the tumor tissue type and its size, and the particular chemotherapeutic agent selected. The amount is any effective amount and can be readily determined by those skilled in the art.

A preferred category of multiple drug resistant tumor cells to be treated by the method of the present invention is multiple drug resistant cells characterized by the multidrug transporter—mediated pumping of antineoplastic agents out of the tumor cells. The multidrug transporter protein is described in M. Gottesman and I. Pastan, *J. Biol. Chem.* 263:12163 (1988). Thus, tumor cells treated by the present invention are preferably those characterized by (a) the expression of the multidrug transporter protein at high levels, or (b) the ability to express the multidrug transporter protein upon exposure to an antineoplastic agent, and/or (c) being glucocorticoid sensitive.

Exemplary tumor cells which express the multidrug transporter at high levels (intrinsically resistant cells) are adenocarcinoma cells, pancreatic tumor cells, carcinoid tumor cells, chronic myelogenous leukemia cells in blast crisis, and non-small cell lung carcinoma cells.

Exemplary tumor cells having the ability to express the multidrug transporter protein upon exposure to an antineoplastic agent are neuroblastoma cells, pheochromocytoma cells, adult acute lymphocytic leukemia cells, adult acute nonlymphocytic leukemia cells, nodular poorly differentiated lymphoma cells, breast cancer cells and ovarian cancer cells.

A preferred group of tumor cells for treatment in accordance with the present invention are lymphomas and leukemias, because such cells are susceptible to treatment with glucocorticoid receptor agonists, and are capable of generating multidrug resistant cells if not treated with chemosensitizer.

Preferred antineoplastic agents for use in the present invention are those which induce multidrug resistance in cells. Exemplary of such antineoplastic agents are vinca alkaloids, epipodophyllotoxins, anthracycline antibiotics, actinomycin D, plicamycin, puromycin, gramicidin D, taxol, colchicine, cytochalasin B, emetine, maytansine, and amsacrine (or "mAMSA") . Preferred are vinca alkaloids, epipodophyllotoxins, anthracycline antibiotics, actinomycin D, and plicamycin.

The vinca alkaloid class is described in *Goodman and Gilman's The Pharmacological basis of Therapeutics*, 1277–1280 (7th ed. 1985) (hereafter "Goodman and Gilman"). Exemplary of vinca alkaloids are vincristine, vinblastine, and vindesine.

The epipodophyllotoxin class is described in Goodman and Gilman, supra at 1280–1281. Exemplary of epipodophyllotoxins are etoposide, etoposide orthoquinone, and teniposide.

The anthracycline antibiotic class is described in Goodman and Gilman, supra at 1283–1285. Exemplary of anthracycline antibiotics are daunorubicin, doxorubicin, mitoxantraone, and bisanthrene. Daunorubicin and doxorubicin are preferred.

Actinomycin D, also called Dactinomycin, is described in Goodman and Gilman, supra at 1281–1283. Plicamycin, also called mithramycin, is described in Goodman and Gilman, supra at 1287–1288.

In accordance with another embodiment of the present invention, there is provided a method of concurrently activating glucocorticoid-induced response and enhancing the intracellular accumulation of a chemotherapeutic agent within a cell. Presently preferred molecules for transport by this method are those molecules which do not naturally occur in such cell, but which are capable of entering such cell (such as, for example, chemotherapeutic agents as described herein). This method comprises contacting the cell with:

a) a quantity of the above-described MDR-reducing compounds sufficient to inhibit transport of the chemotherapeutic agent away from a cellular target of said agent; and b) a chemotherapeutic agent so as to effect interaction of said agent with its intracellular target.

In accordance with the practice of the present invention, molecules for which one might seek to inhibit transport away from a cellular target thereof include taxol, cytochalasin B, gramicidin D, ethidium bromide, emetine, mitomycin, etoposide, tenoposide, vincristine, vinblastine, coltricin, doxirubicin, daunorubicin, dihydroxy anthracin dione, mitoxantrone, mithramycin, actinomycin D, prednisolone, dexamethasone, procaine, tetracaine, lidocaine, propraolol, puromycin, and the like.

As used herein the term "inhibit transport away from a cellular target thereof" means increasing the level of the molecule available for contact with the cellular target of said agent by preventing the transport of the molecule by the P-glycoprotein efflux pump.

Preferred cell types for treatment in accordance with this embodiment of the present invention include tumor cells, especially lymphoid tumor cells.

In accordance with yet another aspect of the present invention the use of the above-described compounds, or pharmaceutically acceptable formulations thereof, for a variety of applications is provided, such as, for example, in the manufacture of a medicament for enhancing the therapeutic effect of an antineoplastic agent, for the manufacture of a medicament for inhibiting multiple drug resistance in tumors, for the manufacture of a medicament for increasing the sensitivity of a resistant tumor to an antineoplastic agent and/or for the manufacture of a medicament for selectively inhibiting the growth of tumor cells.

The invention will now be described in greater detail by reference to the following non-limiting examples.

EXAMPLE 1

Cell Staining Method to Determine Cell Growth

Equal numbers of cells of an anchorage dependent mammalian cell line are seeded in growth medium (e.g., alpha MEM plus 10% FBS) into a suitable culture vessel, e.g., plastic 96 well tissue culture plates. A cytotoxic drug (e.g. doxorubicin) is added to the cells in the dishes at various concentrations, typically ranging between 0 and 100 μM.

Following about 72 hours of continuous exposure to the cytotoxic agent, the growth medium is decanted and the cells are washed with a suitable buffer, e.g., phosphate buffered saline (PBS). About 2 ml of a solution of 2% methylene blue (methylene blue is dissolved in a solution of about 50% ethanol in water) is added to the cells on the dishes. The dye is allowed to contact the cells for about 2 minutes. Excess dye is washed away with cold water and the plates are air dried. The dye stained cells are then solubilized by adding an equal volume of a solution of a detergent, e.g., 1% N-lauroyl-sarcosine, to all wells.

The amount of dye remaining in the wells directly correlates with the number of cells in the well. The amount of methylene blue dye in the wells can be measured spectrophotometrically by measuring absorbance at 600 nm using an electronic ELISA plate spectrophotometer (Minireader II, Dynatech Laboratories, Alexandria, Va.). Typical results show decreased absorbance at 600 nm with increasing cytotoxic drug concentration, indicating increased cell death with increased drug concentration.

EXAMPLE 2

Visual Assay of Multidrug Resistance

Multidrug resistance has been detected in vitro in single cell suspensions and in cell monolayers. Yoshimura et al., Cancer Letters 50:45 (1990) used the accumulation of rhodamine dye to screen for agents that overcome multidrug resistance in a cell line ("reversing agents"). The dye is accumulated in multidrug-resistant cells at a lower rate than it is accumulated in non-resistant cells. Thus multidrug-resistant cells can be distinguished from non-resistant cells by comparing intracellular dye levels.

Dye levels in multidrug-resistant cells are then monitored in the presence and absence of verapamil, a known chemosensitizer (reversing agent used in chemotherapy to facilitate the uptake of a chemotherapeutic drug in drug-resistant tumor cells). It is typically found that the dye accumulates to normal levels when the multidrug resistance phenotype is reversed with verapamil. The dye is administered to cells in a confluent monolayer. The cells are then either washed, solubilized, and the dye detected with a fluorescence spectrometer, or scanned in microtitre wells with a fluorescence microplate reader.

Etferth et al., Arzneim-Forsch 38:1171 (1988) have also developed an in vitro assay to detect the multidrug resistance phenotype. They describe comparing the levels of rhodamine dye in a cell sample with the levels of dye found in a control sample of normal cells. The dye is detected by forming a single cell suspension, pipetting the suspension onto slides, administering the dye to the cells on the slide, and detecting dye uptake of cells on the slide.

Herweijer et al., Invest New Drugs 7:442 (1989) describe the use of on-line flow cytometry to detect cells with the multidrug resistance phenotype in a single cell suspension. The accumulation kinetics of a fluorescent drug are measured on line, first in the absence, and then in the presence of a reversing agent.

Konen et al., J. Histochem. Cytochem. 37:1141 (1989), describe assaying efflux activity of the multidrug resistance transport system using fluorescence microscopy to monitor the accumulation of drugs in single cultured cells that were transformed with multidrug resistance DNA. They showed that the efflux pathway was inhibited when the cells were incubated with verapamil.

EXAMPLE 3

Synthesis of Invention Compounds Having Dual Ability to Reverse Multidrug Resistance and Act as Glucocorticoid Agonists 1,4-Pregnadien-9α-fluoro-16α-methyl-11β,21-diol-3, 20-dione (also known as 17-deoxydexamethasone, or 17-DOD) and 1,4-pregnadiene-9α,11β-dichloro-17α-21-diol-3,20-dione (also known as dichlorisone) were purchased from Steraloids, Inc. All chemicals employed in the following syntheses were purchased from Aldrich Chemical Co. Separation of synthesized compounds was carried out on Silica gel (Merck, 230–400 mesh) column with chloroform containing 0.5–1.0% of ethanol. The progress of the performed reactions and separation patterns were monitored using TLC on Silica gel plates GHLF (Analtech, Inc.) with chloroform+ethyl acetate+ethanol (5:1:0.0) as a solvent system. Developed chromatograms were detected with short wave UV lamp.

The Steglich esterification method, which employs 1,3-Dicyclohexylcarbodiimide and 4-Dimethylaminopyridine as a nucleophilic catalyst in a group transfer reaction, was employed for the formation of C-21 benzoates (Neises and Steglich, Agnew. Chem., mnt. Ed. Engl. 17:522–524 (1978) and Neises and Steglich, W. Org. Synth. 63:183–187 (1984)). The esterification rate of appropriate sterols with this method was a function of steric hindrance; only the formation of C-21 benzoates was observed. Esterification using 3,4-dimethoxybenzoic acid proceeded without any problems and was only time dependent for the appropriate sterol. In the case of 4-dimethlaminobenzoic acid, the formation of non-reactive N-acylcyclohexylurea, instead of O-acylcyclohexylurea was observed. This undesired effect was eliminated by using 4-dimethylaminopyridine hydrochloride as a proton-transfer agent (Boden and Keck, J. Org. Chem. 50:2394–2395 (1985)).

Conversion of 1,4-Pregnadien-9α-fluoro-16α-methyl-11 β,21-diol-3,20-dione to the 21-(N-benzylcarbamate) was based on a typical procedure using benzyl isocyanate in the presence of pyridine (Agawal and Khorana, J. Am. Chem. Soc. 94:3578 (1972)).

Deoxygenation of the 21-hydroxy group in 1,4-Pregnadien-9α-fluoro-16α-methyl-11β,21-diol-3,20-dione was performed according to the Barton free radical reduction of 21-O'- (4-fluorophenyl) thionocarbonate using hypophosphorous acid triethylamine salt as a hydrogen donor (Barton et al., Tetrahedron 48:7435–7446 (1992) and Barton et al., Tetrahedron Lett. 33:5709–5712 (1992)). This free radical reaction was initiated with azoisobutyronitrile, which in mild conditions provided the desired 1,4-pregnadien-9α-fluoro-16 α-methyl-11β-ol-3,20-dione in high yield.

Deoxygenation at C-21 position of 1,4-pregnadiene-9 α,11β-dichloro-17α-21-diol-3,20-dione in the same reaction condition generated a complex mixture.

1, 4-Pregnadien-9α-fluoro-16α-methyl-11β,21-diol-3,20-dione, 21-(3 ,4-dimethoxybenzoate) (SA-43)

A mixture of 1, 4-pregnadien-9α-fluoro-16α-methyl-11β, 21-diol-3,20-dione 10 mg (0.026 mmol) , 3,4-dimethoxy benzoic acid 10 mg (0.05 mmol) and dimethylaminopyridine 5 mg (0.04 mmol) in 0.5 mL of acetonitrile was treated with dicyclohexylcarbodiimide 0.05 mL (10M in $CH_2Cl_2$, 0.05 mmol). After 2.5h reaction at room temperature, TLC analysis showed complete conversion to the target compound. Precipitated dicyclohexylurea was removed by filtration. The filtrate was diluted in ethyl acetate, washed with 0.5M hydrochloric acid and then with saturated sodium bicarbonate. The organic solution was dried over anhydrous sodium sulfate and evaporated to dryness. The oily residue was transferred to a Silica gel column and separated with chloroform containing 0.5–1% of Ethanol. The final product (JZ-43) was crystallized from benzene+ethyl acetate.
1,4-Pregnadien-9α11β-dichloro-17α,21-diol-3,20-dione, 21-(3,4-dimethoxybenzoate) (SA-44)

To the mixture of 1,4-pregnadien-9α,11β-dichloro-17 α,21-diol-3,20-dione 20 mg (0.048 mmol), 3,4-dimethoxy benzoic acid 20 mg (0.1 mmol) and dimethylaminopyridine 10 mg (0.08 mmol) in 2 mL of tetrahydrofuran dicyclohexylcarbodiimide 0.1 ml (1.0M in $CH_2Cl_2$ 0.1 mmol) was added.

The reaction progress at room temperature was monitored by TLC. After two days, the esterification was complete. Product was then isolated from the reaction mixture in the same manner as described above. An analytical sample of JZ-44 was crystallized from ethyl acetate+ether.

1,4-Pregnadien-9α-fluoro-16αmethyl-11β,21-diol-3 20-dione, 21-(4-dimethylaminobenzoate) (SA-45)

A mixture of 1,4-pregnadien-9αfluoro-16αmethyl-11 β,21-diol-3,20-dione 20 mg (0.053 mmol), 4-dimethylamino benzoic acid 16.5 mg (0.1 mmol), 4-dimethylaminopyridine 10 mg (0.08 mmol), 4-dimethylaminopyridine hydrochloride 8 mg (0.05 mmol) in 0.7 mL of acetonitrile was treated with dicyclohexylcarbodiimide 0.1 mL (1.0M in $CH_2Cl_2$, 0.1 mmol). The reaction was completed overnight at room temperature and the product was isolated as described above. Crystallization from ethyl acetate+ether gave the final form of JZ-45.

1,4-Pregnadien-9α,11β-dichloro-17α,21-diol-3,20-dione, 21-(4-dimethylaminogenzoate) (SA-47)

This esterification required much stronger reaction conditions than the previously described reactions (i.e., higher molar ratio, higher reaction temperatures, etc.). A mixture of 1,4-pregnadien-9α,11β-dichloro-17α,21-diol-3,20-dione 20 mg (0.048 mmol), 4-dimethylaminobenzoic acid 25 mg (0.15 mmol), 4-dimethylaminopyridine 15 mg (0.12 mmol), 4-dimethyloaminopyridine hydrochloride 12 mg (0.075 mmol) in 2 mL of tetrahydrofuran was treated with dicyclohexylcarbodiimide 0.15 mL (1.0M in $CH_2Cl_2$, 0.15 mmol). The reaction was complete after 24 h at 40°–45° C. The product was then isolated in a similar manner to that described above. Crystallization from methanol gave an analytical sample of JZ-47.

1. 4-Preqnadien-9αfluoro-16αmethyl-11β,21-diol-3 20-dione, 21-(N-benzylcarbamate) (SA-54)

To the 1,4-pregnadien-9αfluoro-16αmethyl-11 β,21-diol-3,20-dione 10 mg (0.026 mmol) in 0.1 mL of pyridine was added benzylisocyanate 0.007 ml (0.05 mmol). The reaction mixture was kept at 40° C. for 2 h. After this time the reaction mixture was evaporated to dryness under vacuum and the residue separated on a Silca gel column with chloroform containing 0.5–1% ethanol. The final product was crystallized from ethyl acetate+ether.

1, 4-Pregnadien-9αfluoro-16αmethyl-11β-ol-3 20-dione, (SA-50)

1,4-Pregnadien-9αfluoro-16αmethyl-11β-21-diol-3,20-dione, 21-0'-(4-fluorophenyl)thionocarbonate was prepared as follows:

1,4-pregnadien-9αfluoro-16αmethyl-11β,21-diol-3,20-dione 20 mg (0.053 mmol) and pyridine 0.005 ml (0.06 mmol) in 0.1 mL of dichloromethane was treated with 4-fluorophenyl chloroformate. After 0.5 h at room temperature, the reaction mixture was evaporated to dryness under vacuum. Crystallization of the residue from ether provided the desired compound.

Water was removed from hypophosphorous acid (as a 50% aqueous solution (0.055 ml; 0.53 mmol) by evaporation under vacuum. The residue was dissolved in 0.3 mL of dioxane and triethylamine 0.081 mL (0.58 mmol) was added. To this solution was added the 21-0'-(4-fluorophenyl) thionocarbonate and 1,1'-azobis(cyclohexanecarbonitrile) 2 mg (0.008 mmol) prepared as described above. The reaction mixture was heated up to 100° C. for 0.5 h under nitrogen. TLC analysis showed complete conversion to the target compound. The reaction mixture after evaporation was separated on Silica gel column and the final product was crystallized from methanol.

EXAMPLE 4

Evaluation of Glucocorticoid Agonist Activity of Various Steroid Analogs

The glucocorticoid agonist activity of several steroid analogs was evaluated by determining the glucocorticoid-

17 induced apoptosis of murine thymoma W7TB cells. Thus, murine W7TB cells were distributed (5×10⁴ cells/ml/well) into multiwell dishes and incubated for 5 days with increasing concentrations of test compound, as indicated in FIG. 1. Dichlorisone is 1,4-pregnadiene-9α, 11β-dichloro-17α-21-diol-3,20-dione; "SA 44" is the 3,4-dimethoxy benzoic acid ester of dichlorisone; and "SA 47" is the 4-dimethylamino benzoic acid ester of dichlorisone. "17-DOD" is 17-deoxydexamethasone (i.e., 1,4-pregnadien-9α-fluoro-16αmethyl-11β,21-diol-3,20-dione); "SA 45" is the 4-dimethylamino benzoic acid ester of 17-DOD; and "SA 54" is the N-benzylcarbamate of 17-DOD.

Figure 1B:
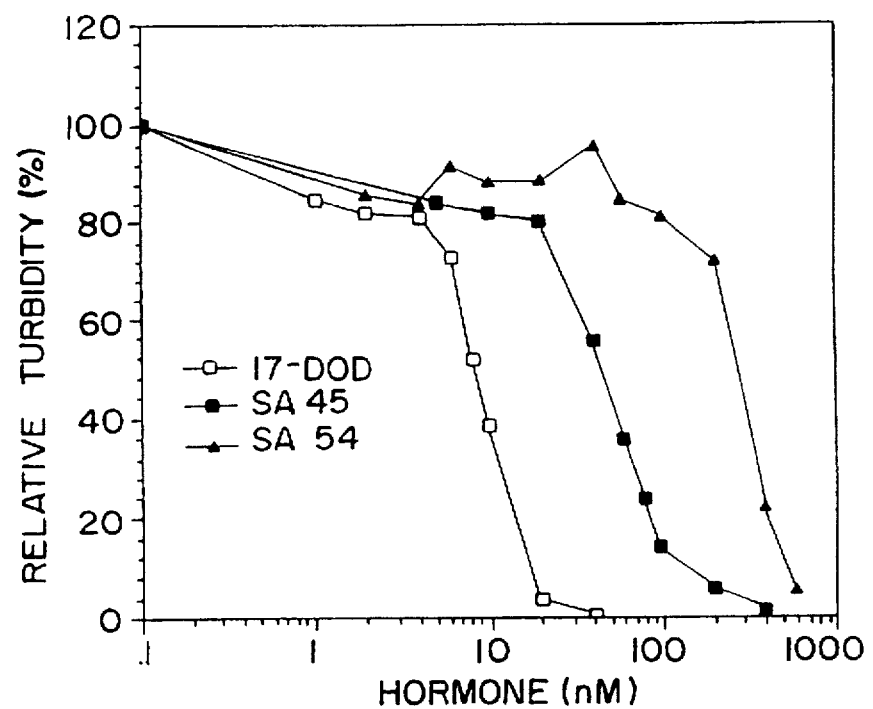
FIG. 1B presents results with the agonist, 17-deoxydexamethasone, as well as 2 derivatives thereof.

At the end of the incubation period, the turbidity values (at 660 nm) for each set of cultures were measured and expressed relative to cells that were incubated without test compound. These values represent the effect of test compound on the relative amount of cell proliferation under a given set of growth conditions. Each value shown in FIGS. 1A and 1B is the average of 2 separate determinations. Results are also presented in the third data column of Table 1, wherein $LD_{50}$ values reflect the agonist concentration that causes the Relative Turbidity value to be reduced to 50%.

EXAMPLE 5

Evaluation of Reversal of MDR by Various Steroid Analogs in Cells Displaying MDR Phenotype I. Reversal of Puromycin Resistance in the S7dex$^r$-1 Cell Line The S7dex$^r$-1 cell line is a glucocorticoid resistant derivative of the S7CD-5 cell line. It was selected on the basis of its resistance to the glucocorticoid agonist triamcinolone acetonide ($5\times10^{-7}$M) from S7CD-5 cells that had been mutagenized with N-methyl-N'-nitro-N-nitrosoguanidine. The apoptic response to glucocorticoid agonists is not elicited in the S7dex$^r$-1 cells. Thus, murine S7dex$^r$-1 cells were distributed (5×10⁴ cells/ml, 1 ml/well) into multiwell dishes and incubated for 5 days with 20 µM puromycin and increasing concentrations of test compound. At the end of the incubation period, the turbidity values (at 660 nm) for each set of cultures were measured and expressed relative to cells that were incubated without test compound. These values represent the ability of test compound to reverse S7dex$^r$-1 resistance to 20 µM puromycin, as reflected by the relative amount of cell proliferation under a given set of growth conditions. The number of repetitions of each value presented in the first data column of Table 1 are indicated in parenthesis after each entry. In the Table, the $ED_{50}$ values reflect the concentration of chemosensitizer that causes the Relative Turbidity value to be reduced by 50%.

II. Reversal of Vinblastine Resistance in the CEM/VLB$_{100}$ Cell Line

Figure 2A:
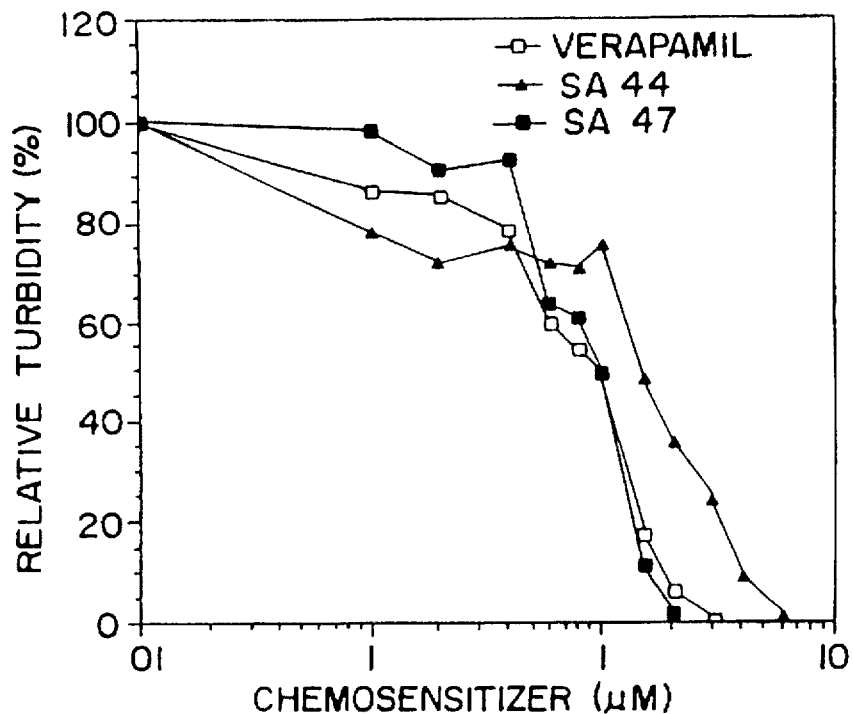
FIG. 2A presents results with the reversing agent, verapamil, as well as two derivatives of dichlorisone.
Figure 2B:
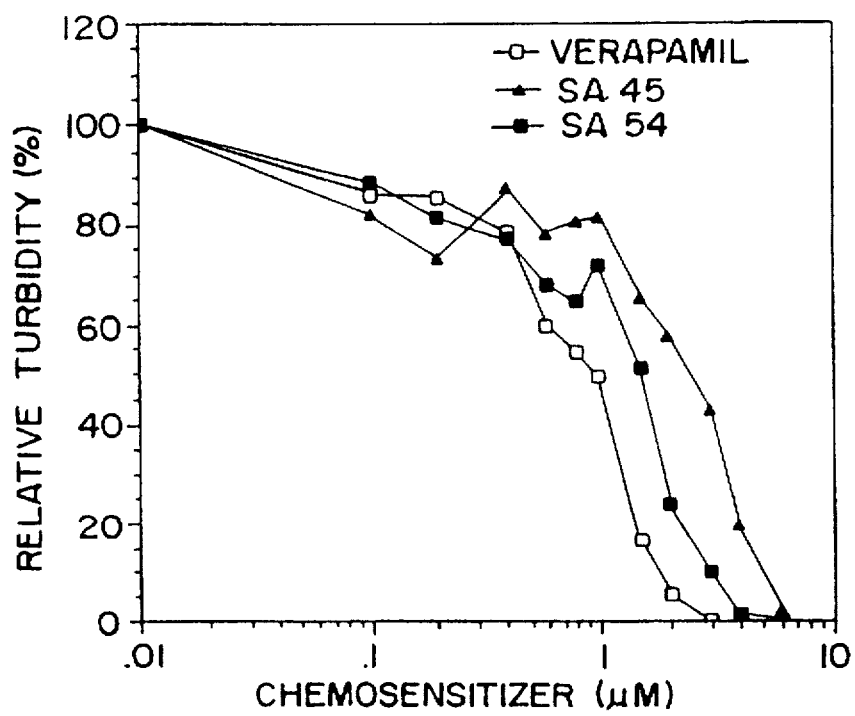
FIG. 2B presents results with the reversing agent, verapamil, as well as two derivatives of 17-deoxydexamethasone.

The CEM/VLB$_{100}$ cell line is a derivative of human CEM cells, selected for resistance to vinblastine. This cell line expresses the human MDR1 gene. CEM/VLB$_{100}$ cells were distributed (5×10⁴ cells/ml, 1 ml/well) into multiwell dishes and incubated for 5 days with 30 nM vinblastine and increasing concentrations of test compound, as indicated in FIG. 2. At the end of the incubation period, the turbidity values (at 660 nm) for each set of cultures were measured and expressed relative to cells that were incubated without test compound. These values represent the ability of test compound to reverse CEM/VLB$_{100}$ resistance to 30 nM vinblastine, as reflected by the relative amount of cell proliferation under a given set of growth conditions. Each value shown in FIG. 2 is the average of 2 separate determinations. Results are also presented in the second data column of Table 1, wherein the $ED_{50}$ values reflect the concentration of chemosensitizer that causes the Relative Turbidity value to be reduced by 50%.

18

| Chemosensitizer | $ED_{50}^1$, (µM) | $ED_{50}^2$, (µM) | $LD_{50}^3$, (nM) |
|---|---|---|---|
| Verapamil | 0.76 (9) | 1.3 (6) | NA* |
| Progesterone | 1.6 (3) | >8.0 (1) | 2,400 (4) |
| Dichlorisone | >8.0 (1) | >8.0 (1) | 7.5 (4) |
| SA 44 | 0.44 (3) | 2.5 (4) | 14 (2) |
| SA 47 | 0.45 (3) | 1.1 (3) | 13 (3) |
| 17-DOD | 2.7 (3) | >8.0 (1) | 5.3 (4) |
| SA 43 | NA | 1.2 (2) | 18 (2) |
| SA 45 | 0.36 (3) | 2.7 (2) | 34 (2) |
| SA 50 | 0.53 (2) | >8.0 (1) | 9.0 (2) |
| SA 54 | 0.42 (2) | 1.8 (3) | 250 (2) |

[1] S7dex-1 cells
[2] CEM/VLB$_{100}$ cells
[3] W7TB cells
*NA = not analyzed

While the invention has been described in detail with reference to certain preferred embodiments thereof, it will be understood that modifications and variations are within the spirit and scope of that which is described and claimed.

That which is claimed is:

1. A method for concurrently activating glucocorticoid-induced response and reducing multidrug resistance in a subject undergoing chemotherapy, comprising administering to said subject, in conjunction with a chemotherapeutic agent, an effective amount of a steroid compound having the dual properties of acting as a glucocorticoid agonist and as an inhibitor of the P-glycoprotein efflux pump, wherein said steroid compound has the structure:

wherein:

$R^9$ is absent when there is a double bond between $C^9$ and $C^{10}$, or when there is an epoxide bridging $C^9$ and $C^{10}$, or when present, $R^9$ is hydrogen or halogen;

$R^{10}$ is absent when there is a double bond between $C^9$ and $C^{10}$, or when there is an epoxide bridging $C^9$ and $C^{10}$, or when present, $R^{10}$ is hydrogen or methyl;

$R^{11}$ is independently hydrogen, alkenyl, alkynyl, halogen, or —OR, wherein R is hydrogen, lower alkyl or trimethylsilyl;

$R^{16}$ is H or methyl, $R^{17}$ is hydrogen, when $R^{20}$ is an organic radical; or $R^{17}$ is —OR' when $R^{20}$ is —C(O)—(CH$_2$)$_q$—Z, wherein R' is hydrogen only if q is greater than 1, or R' is an acyl group having in the range of 3 up to 20 carbon atoms, wherein said acyl group optionally contains one or more atoms selected from the group consisting of oxygen (in addition to the acyl carbonyl oxygen), sulfur, nitrogen, phosphorus, silicon and halogen, wherein said acyl group optionally includes one or more cyclic moieties selected from the group consisting of alicyclic ring(s), heterocyclic ring(s), carbocyclic aromatic ring(s), and heterocyclic aromatic ring(s), wherein said cyclic moiety(ies) optionally contains an oxygen-, sulfur-, nitrogen-, phosphorus- or silicon-bearing substituent; and $R^{20}$ is —C(O)—(CH$_2$)$_q$—Z, wherein q falls in the range of 0 up to 8, and Z is alkyl, hydroxyalkyl, alkoxy, aryl, or halogen, or $R^{20}$ is said organic radical, said organic radical having in the range of 4 up to 20 carbon atoms, wherein said organic radical optionally contains one or more atoms selected from the group consisting of oxygen, sulfur, nitrogen, phosphorus, silicon and halogen, wherein said organic radical optionally includes one or more cyclic moieties selected from the group consisting of alicyclic ring(s), heterocyclic ring (s), carbocyclic aromatic ring(s), and heterocyclic aromatic ring(s), wherein said cyclic moiety(ies) optionally contains an oxygen-, sulfur-, nitrogen-, phosphorus- or silicon-bearing substituent, wherein said cyclic moiety is mandatory when $R^{20}$ is linked to $C^{17}$ through a —C(O)—moiety.

2. A method according to claim 1 wherein $R^{20}$ includes one or more rings independently selected from the group consisting of carbocyclic aromatic ring(s) and heterocyclic aromatic ring(s).

3. A method according to claim 2 wherein said heterocyclic aromatic ring contains at least one oxygen-, sulfur-, nitrogen-, phosphorus- or silicon-bearing substituent.

4. A method according to claim 1 wherein $R^{20}$ is

—C(O)—CH$_2$—O—C(O)—(CH$_2$)$_q$—Ar or

—C(O)—CH$_2$—O—C(O)—NH—(CH$_2$)$_q$—Ar, wherein q falls in the range of about 0 up to 8 and Ar is N-methyl piperazine or:

—(C$_6$H$_x$)—[X$_{0,1}$—(CH$_2$)$_y$—X']$_z$ wherein:

x is 2–5, y is 0–2, z is 0 when x is 5, or 1 when x is 4, or 2 when x is 3, or 3 when x is 2, X is O or S, and X' is R when y is 0, wherein R is as defined above, or X' is hydrogen, OR, NR"$_2$, N$^+$R"$_3$,

or NO$_2$, when y is 1 or 2, wherein R is as defined above and R" is hydrogen or lower alkyl.

5. A method according to claim 4 wherein Ar is phenyl, 3,4-dimethoxyphenyl, 3,4,5-trimethoxyphenyl, 4-dimethylaminophenyl, or N-methyl piperazine.

6. A method according to claim 4 wherein z is 1, and the substituent on the phenyl ring is located at the para position of the ring.

7. A method according to claim 6 wherein the substituent on the phenyl ring is:

—O—CH$_2$CH$_2$—NR"$_2$,

—O—CH$_2$CH$_2$—N$^+$R"$_3$, or

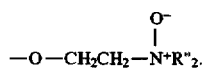

—O—CH$_2$CH$_2$—N$^+$R"$_2$.

8. A method according to claim 4 wherein z is 2, and the substituents on the phenyl ring are located at the meta and para positions of the ring.

9. A method according to claim 8 wherein the para substituent is —OR, —NR"$_2$, —N$^+$R"$_3$,

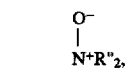

or —NO$_2$.

10. A method according to claim 1 wherein $R^{20}$ is

—(CH$_2$)$_x$—CR"=CR"—(CH$_2$)$_x$—X"

or

—(CH$_2$)$_x$—C≡C—(CH$_2$)$_x$—X", wherein R" is hydrogen or lower alkyl, and X" is hydrogen, chloro, trimethylsilyl or a cyclic moiety selected from the group consisting of an optionally substituted alicyclic ring, heterocyclic ring, carbocyclic aromatic ring, and heterocyclic aromatic ring, and each x is independently selected from 0–6, with the proviso that $R^{20}$ contain at least 6 carbon atoms.

11. A method according to claim 1 wherein $R^{20}$ is —C(O)—(CH$_2$)$_q$—Z, wherein q falls in the range of 0 up to 8, and Z is alkyl, hydroxyalkyl, alkoxy, aryl or halogen, and $R^{17}$ is —OR', wherein R' is —C(O)—(CH$_2$)$_q$—Ar or —C(O)—NH—(CH$_2$)$_q$—Ar, wherein q falls in the range of about 0 up to 8 and Ar is:

—(C$_6$H$_x$)—[X$_{0,1}$—(CH$_2$)$_y$—X']$_z$ wherein:

x is 2–5, y is 0–2, z is 0 when x is 5, or 1 when x is 4, or 2 when x is 3, or 3 when x is 2, X is O or S, and X' is R when y is 0, wherein R is as defined above, or X' is hydrogen, OR, NR"$_2$, N$^+$R"$_3$,

or NO$_2$, when y is 1 or 2, wherein R is as defined above and R" is hydrogen or lower alkyl.

12. A method according to claim 1 wherein $R^9$ is a halogen.

13. A method according to claim 1 wherein $R^{10}$ is methyl.

14. A method according to claim 1 wherein $R^{11}$ is hydrogen, hydroxy or halogen.

15. A method according to claim 1 wherein $R^{16}$ is methyl.

16. A method according to claim 4 wherein $R^{17}$ is selected from hydrogen or hydroxy.

17. A method according to claim 1 wherein said compound contains a double bond between $C^1$ and $C^2$.

18. A method according to claim 1 wherein said compound contains a double bond between $C^9$ and $C^{10}$.

19. A method according to claim 1 wherein:

$R^9$ is fluorine;

$R^{10}$ is methyl;

$R^{11}$ is hydroxy;

$R^{16}$ is methyl;

$R^{17}$ is hydrogen; and $R^{20}$ is:

—C(O)—CH$_2$—O-C(O)—(CH$_2$)$_q$—Ar or

21

—(O)—CH$_2$—O—C(O)—NH—(CH$_2$)$_q$—Ar, wherein Ar is phenyl, 3,4-dimethoxyphenyl, 3,4,5-trimethoxyphenyl, 4-dimethylaminophenyl, or N-methyl piperazine, and q falls in the range of about 0 up to 8.

20. A method according to claim 1 wherein:
R$^9$ and R$^{11}$ are each chlorine;
R$^{10}$ is methyl;
R$^{16}$ is methyl;
R$^{17}$ is hydroxy; and
R$^{20}$ is:

—C(O)—CH$_2$—O—C(C)—(CH$_2$)$_q$—Ar or

—C(O)—CH$_2$—O—C(O)—NH—(CH$_2$)$_q$—Ar, wherein Ar is phenyl, 3,4-dimethoxyphenyl, 3,4,5-trimethoxyphenyl, 4-dimethylaminophenyl, or N-methyl piperazine, and q falls in the range of about 0 up to 8.

21. A method according to claim 1 wherein said compound is administered orally, percutaneously, parenterally, rectally or by inhalation.

22. A method of concurrently activating glucocorticoid-induced response and enhancing the accumulation of a chemotherapeutic agent within a cell, said method comprising contacting the cell with
(a) a quantity of a compound sufficient to inhibit transport of the chemotherapeutic agent away from a cellular target of said agent, and
(b) a chemotherapeutic agent so as to effect interaction of said agent with its intracellular target;
wherein said compound has the structure:

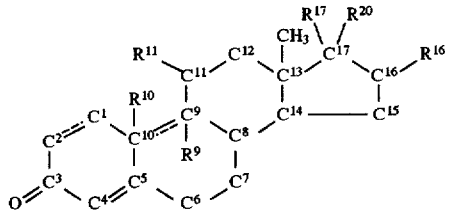

wherein:
R$^9$ is absent when there is a double bond between C$^9$ and C$^{10}$, or when there is an epoxide bridging C$^9$ and C$^{10}$, or when present, R$^9$ is hydrogen or halogen;

22

R$^{10}$ is absent when there is a double bond between C$^9$ and C$^{10}$, or when there is an epoxide bridging C$^9$ and C$^{10}$, or when present, R$^{10}$ is hydrogen or methyl;

R$^{11}$ is independently hydrogen, alkenyl, alkynyl, halogen, or —OR, wherein R is hydrogen, lower alkyl or trimethylsilyl;

R$^{16}$ is H or methyl,

R$^{17}$ is hydrogen, when R$^{20}$ is an organic radical; or

R$^{17}$ is —OR' when R$^{20}$ is —C(O)—(CH$_2$)$_q$—Z, wherein R' is hydrogen only if q is greater than 1, or R' is an acyl group having in the range of 3 up to 20 carbon atoms, wherein said acyl group optionally contains one or more atoms selected from the group consisting of oxygen (in addition to the acyl carbonyl oxygen), sulfur, nitrogen, phosphorus, silicon and halogen, wherein said acyl group optionally includes one or more cyclic moieties selected from the group consisting of alicyclic ring(s), heterocyclic ring(s), carbocyclic aromatic ring(s), and heterocyclic aromatic ring(s), wherein said cyclic moiety(ies) optionally contains an oxygen-, sulfur-, nitrogen-, phosphorus- or silicon-bearing substituent; and R$^{20}$ is —C(O)—(CH$_2$)$_q$—Z, wherein q falls in the range of 0 up to 8, and Z is alkyl, hydroxyalkyl, alkoxy, aryl, or halogen, or R$^{20}$ is said organic radical, said organic radical having in the range of 4 up to 20 carbon atoms, wherein said organic radical optionally contains one or more atoms s elected from the group consisting of oxygen, sulfur, nitrogen, phosphorus, silicon and halogen, wherein said organic radical optionally includes one or more cyclic moieties selected from the group consisting of alicyclic ring(s), heterocyclic ring(s), carbocyclic aromatic ring(s), and heterocyclic aromatic ring(s), wherein said cyclic moiety(ies) optionally contains an oxygen-, sulfur-, nitrogen-, phosphorus- or silicon-bearing substituent, wherein said cyclic moiety is mandatory when R$^{20}$ is linked to C$^{17}$ through a —C(O)— moiety.

23. A method according to claim 22 wherein the cell is a tumor cell.

24. A method according to claim 23 wherein said tumor cell is a hematopoeitic cell.

* * * * *